United States Patent [19]

Huss, Jr. et al.

[11] Patent Number: 4,992,615

[45] Date of Patent: Feb. 12, 1991

[54] ISOPARAFFIN-OLEFIN ALKYLATION PROCESS

[75] Inventors: Albin Huss, Jr., Chadds Ford, Pa.; Garry W. Kirker, Washington Township, Glouchester County, N.J.; Kathleen M. Keville, Woodbury, N.J.; Robert T. Thomson, Voorhees, N.J.

[73] Assignee: Mobil Oil Corp., Fairfax, Va.

[21] Appl. No.: 470,014

[22] Filed: Jan. 25, 1990

[51] Int. Cl.$^5$ .................................................. C07C 2/58
[52] U.S. Cl. .................................... 585/722; 585/726
[58] Field of Search ............................... 585/722, 726

[56] References Cited

U.S. PATENT DOCUMENTS

| | | | |
|---|---|---|---|
| 2,363,116 | 11/1944 | Bruner | 260/683.4 |
| 2,843,642 | 7/1958 | Kelly | 260/683.44 |
| 2,939,890 | 6/1960 | Hervert et al. | 260/671 |
| 3,131,230 | 4/1964 | Hervert et al. | 260/671 |
| 3,251,902 | 5/1966 | Garwood et al. | 585/722 |
| 3,450,644 | 6/1969 | Lanewale et al. | 252/416 |
| 3,541,180 | 11/1970 | Thomas | 260/683.43 |
| 3,549,557 | 12/1970 | Bocton et al. | 585/722 |
| 3,624,173 | 11/1971 | Kirsch et al. | 585/722 |
| 3,644,565 | 2/1972 | Biace | 585/722 |
| 3,647,916 | 3/1972 | Caesar et al. | 585/722 |
| 3,655,813 | 6/1972 | Kirsch et al. | 585/722 |
| 3,706,814 | 12/1972 | Kirsch et al. | 260/683.43 |
| 3,738,977 | 6/1973 | Biale | 260/94.9 |
| 3,840,613 | 10/1974 | Eberly, Jr. et al. | 260/683.43 |
| 3,855,342 | 12/1974 | Huang et al. | 260/683.44 |
| 3,862,258 | 1/1975 | Huang et al. | 260/683.44 |
| 3,865,894 | 2/1975 | Kirsch et al. | 585/722 |
| 3,893,942 | 7/1975 | Yang | 585/722 |
| 3,917,738 | 11/1975 | Fenske et al. | 585/722 |
| 4,300,015 | 11/1981 | Kirsch et al. | 585/722 |
| 4,377,721 | 3/1983 | Crester et al. | 585/722 |
| 4,384,161 | 5/1983 | Huang | 585/722 |
| 4,385,195 | 5/1983 | Batter et al. | 585/722 |
| 4,439,409 | 3/1984 | Pappe et al. | 423/329 T |
| 4,665,264 | 5/1987 | Rodeward et al. | 585/722 |
| 4,826,667 | 5/1989 | Zones et al. | 423/277 |
| 4,836,911 | 6/1989 | Skeels et al. | 585/467 |

FOREIGN PATENT DOCUMENTS 0231860 8/1987 European Pat. Off. .
0293032 11/1988 European Pat. Off. .

*Primary Examiner*—Patrick P. Garvin
*Assistant Examiner*—George R. Fourson
*Attorney, Agent, or Firm*—Alexander J. McKillop; Charles J. Speciale; Dennis P. Santini

[57] ABSTRACT

The alkylation of isoparaffin with olefin to provide alkylate is carried out in the presence of, as catalyst, a porous crystalline material characterized by an X-ray diffraction pattern including interplanar d-spacings at $12.36\pm0.4$, $11.03\pm0.2$, $8.83\pm0.14$, $6.18\pm0.12$, $6.00\pm0.10$, $4.06\pm0.07$, $3.91\pm0.07$ and $3.42\pm0.06$ Angstroms.

24 Claims, No Drawings

ISOPARAFFIN-OLEFIN ALKYLATION PROCESS

BACKGROUND OF THE INVENTION

The present invention relates to an isoparaffin-olefin alkylation process carried out in the presence of, as catalyst, a zeolite of a particular type to provide an alkylate product useful, inter alia, as an octane enhancer for gasoline.

As a result of the curtailment in the use of tetraethyl lead as an octane-improving additive for gasoline, not only has the production of unleaded gasoline increased but the octane number specification of all grades of gasoline have increased as well. Isoparaffin-olefin alkylation is a key route to the production of highly branched paraffin octane enhancers which are to be blended into gasolines.

Alkylation involves the addition of an alkyl group to an organic molecule. Thus, an isoparaffin can be reacted with an olefin to provide an isoparaffin of higher molecular weight. Industrially, alkylation often involves the reaction of $C_2$-$C_5$ olefins with isobutane in the presence of an acidic catalyst. Alkylates are valuable blending components for the manufacture of premium gasolines due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88-94 percent by the continuous addition of fresh acid and the continuous withdrawal of spent acid. The hydrofluoric acid process is less temperature-sensitive and the acid is easily recovered and purified.

The typical types of alkylation currently used to produce high octane gasoline blending component, that is, the hydrofluoric acid and sulfuric acid alkylation processes, have inherent drawbacks including environmental concerns, acid consumption and disposal of corrosive materials. With the increasing demands for octane and the increasing environmental concerns, it has been desirable to develop an alxylation process based on a solid catalyst system. The catalyst of the present invention offers a refiner a more environmentally acceptable alkylation process than the currently used hydrofluoric and sulfuric acid alkylation processes.

Crystalline metallosilicates, or zeolites, have been widely investigated for use in the catalysis of isoparaffin alkylation. For example, U.S. Pat. No. 3,251,902 describes the use of a fixed bed of ion-exchanged crystalline aluminosilicate having a reduced number of available acid sites for the liquid phase alkylation of $C_4$-$C_{20}$ branched-chain paraffins with $C_2$-$C_{12}$ olefins. The patent further discloses that the $C_4$-$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$-$C_3$ olefins using certain crystalline aluminosilicate zeolite catalysts in a fixed, moving or fluidized bed system, the olefin being preferably injected at various points in the reactor.

U.S. Pat. No. 3,644,565 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin mole ratios below 3:1 and regeneration of the catalyst.

U.S. Pat. No. 3,655,813 discloses a process for alkylating $C_4$-$C_5$ isoparaffins $C_3$-$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,893,942 describes an isoparaffin alkylation process employing, as catalyst, a Group VIII metal-containing zeolite which is periodically hydrogenated with hydrogen in the gas phase to reactivate the catalyst when it has become partially deactivated.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite-catalyzed isoparaffin-olefin alkylation process and further provides for the addition of $C_5$+paraffins such as Udex raffinate or $C_5$+olefins to the alkylation reactor feed and the use of specific reactant proportions, halide adjuvants, etc.

U.S. Pat. No. 3,624,173 discloses the use, in isoparaffin-olefin alkylation, of zeolite catalysts containing gadolinium.

U.S. Pat. No. 3,738,977 discloses alkylation of paraffins with ethylene employing a zeolite catalyst which possesses a Group VIII metal component, the catalyst having been pretreated with hydrogen.

U.S. Pat. No. 3,865,894 describes the alkylation of $C_4$-$C_6$ isoparaffin with $C_3$-$C_9$ monoolefin employing a substantially anhydrous acidic zeolite, for example acidic zeolite Y (zeolite HY), and a halide adjuvant.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption is said to prevent polymerization of the olefin during alkylation.

U.S. Pat. No. 4,377,721 describes an isoparaffin- olefin alkylation process utilizing, as catalyst, ZSM-20, preferably HZSM-20 or rare earth cation-exchanged ZSM-20.

U.S. Pat. No. 4,384,161 describes a process of alkylating isoparaffins with olefins to provide alkylate employing as catalyst a large pore zeolite capable of absorbing 2,2,4-trimethylpentane, e.g., ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite in combination with a Lewis acid in accordance with this patent is reported to greatly increase the activity and selectivity of the zeolite thereby effecting alkylation with high olefin space velocity and low isoparaffin/olefin ratio.

SUMMARY OF THE INVENTION

In accordance with the present invention, isoparaffin-olefin alkylation is carried out employing, as catalyst, a synthetic porous crystalline material, or zeolite, which is characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

Isoparaffin-light olefin alkylation plays an important role in the manufacture of high octane gasoline blending stocks with alkylate typically comprising 10–15% of the gasoline pool. Alkylate is an especially valuable component of the gasoline pool as it possesses both high research and motor octane (low sensitivity) numbers, contains no olefins or aromatics and little or no sulfur, demonstrates excellent stability and is clean burning. One measure of the selectivity of an alkylation catalyst is the $C_9+$ yield. This fraction generally results from oligomerization of the feed olefins resulting in a loss of alkylate yield, reduced alkylate quality and the possible formation of an acidic sludge fraction. The zeolite alkylation catalyst employed in the process of this invention provides reduced $C_9+$ yields relative to such known zeolite alkylation catalysts as zeolite HY, e.g., as disclosed in U.S. Pat. No. 3,865,894 referred to above.

The alkylate produced by the process of this invention is of high quality based on both research and motor octane numbers and as such is particularly well suited for blending into the gasoline pool.

DESCRIPTION OF SPECIFIC EMBODIMENTS

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
|---|---|
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | W–S |
| 3.91 ± 0.07 | M–VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | W–S |
| 3.91 ± 0.07 | M–VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | W–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | W–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensites, $100 \, I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for isoparaffin-olefin alkylation. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use as alkylation catalyst herein, the catalyst crystals should be subjected to thermal treatment to remove part or all of any organic constituent present therein.

The alkylation catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use as alkylation catalyst in the process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-60 | 10-40 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desired to incorporate the crystalline material with another material, i.e., a binder, which is resistant to the temperatures and other conditions employed in the isoparaffin alkylation process of this invention. Suitable binder materials include active and inactive materials and synthetic or naturally occurring zeolites as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials suitably serve as diluents to control the amount of conversion so that isoparaffin alkylation products can be obtained economically and in a controlled fashion without having to employ other means for controlling the rate of reaction. These materials can be incorporated into naturally occurring clays, e.g., bentonite and kaolin, to improve the crush strength of the zeolite under commercial isoparaffin alkylation operating conditions. Good crush strength is an advantageous attribute for commercial use since it prevents or delays breaking down of the catalyst into powder-like materials.

Naturally occurring clays which can be composited with MCM-22 crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

Apart from or in addition to the foregoing binder materials, the crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the zeolite content ranging from about 1 to about 95 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5-100% steam at a temperature of at least 300° C. (e.g. 300-650° C.) for at least one hour (e.g. 1-200 hours) at a pressure of 100-2, 500 kPa. In a more particular embodiment, the catalyst can be made to undergo steaming with 75-100% steam at 315-500° C. and atmospheric pressure for 2-25 hours.

The operating temperature of the alkylation process herein can extend over a fairly broad range, e.g., from about −25° C. to about 400° C., and is preferably within the range of from about 75° C. to about 200° C. The practical upper operating temperature will often be dictated by the need to avoid an undue occurrence of undesirable side reactions.

The pressures employed in the present process can extend over a considerably wide range, e.g., from subatmospheric pressure to about 5000 psig, and preferably from atmospheric pressure to about 1000 psig.

The amount of zeolite used in the present alkylation process can be varied over relatively wide limits. In general, the amount of zeolite as measured by the weight hourly space velocity (WHSV) based on olefin can range from about 0.01 to about 100 $hr^{-1}$, preferably from 0.1 to 20 $hr^{-1}$. It will, of course, be realized by those skilled in the art that the amount of catalyst selected for a particular reaction will be determined by several variables including the reactants involved as well as the nature of the catalyst and the operating conditions employed.

The isoparaffin reactant used in the present alkylation process is one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant employed herein generally contains from 2 to about 12 carbon atoms. Representative examples are ethylene, propylene, butene-1, butene-2, isobutylene, pentenes, hexenes, heptenes and octenes. Particularly preferred are $C_3$ and $C_4$ olefins and mixtures thereof.

In general, the mole ratio of total isoparaffin to total olefin alkylating agent in the combined hydrocarbon feed can be from about 1:2 to about 100:1 and is preferably in the range of from about 3:1 to about 20:1. The isoparaffin and/or olefin reactants can be in either the vapor phase or the liquid phase and can be neat, i.e., free from intentional admixture of dilution with other material, or the reactants can be brought into contact with the catalyst composition with the aid of carrier gases or diluents such as, for example, hydrogen or nitrogen.

The reactants can be introduced to the alkylation reaction zone together with one or more other materials which serve to enhance the overall conversion operation. Thus, for example, relatively small quantities of hydrogen and/or hydrogen donors can be present in the reaction zone to suppress catalyst aging. Water and/or materials such as alcohols which provide water under the alkylation conditions selected can also be introduced into the reaction zone for this purpose. Oxygen and/or other materials which tend to suppress oligomerization of the olefin feed can be present in the typically very small amounts which are effective to achieve this benefit. The optimum amounts of these optional materials which can be utilized to advantage in a particular alkylation operation can be readily determined by those skilled in the art employing routine experimentation.

The alxylation process of the present invention can be carried out as a batch-type, semi-continuous or continuous operation utilizing a fixed or moving bed of the zeolite catalyst component. A preferred embodiment entails use of a catalyst zone wherein the hydrocarbon charge is passed concurrently or countercurrently through a moving bed of particle-form catalyst. The latter, after use, is conducted to a regeneration zone where coke is removed, e.g., by burning in an oxygen-containing atmosphere (such as air) at elevated temperature or by extracting with a solvent, after which the regenerated catalyst is recycled to the conversion zone for further contact with the organic reactants.

In order to more fully illustrate the alkylation process of this invention and the manner of practicing same, the following examples are presented. In examples illustrative of the synthesis of zeolite, whenever sorption data are set forth for comparison of sorptive capacities for water, cyclonexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclonexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=$0.016 \sec^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:
$SiO_2/Al_2O_3 = 30.0$
$OH^-/SiO_2 = 0.18$
$H_2O/SiO_2 - 44.9$
$Na/SiO_2 = 0.18$
$R/SiO_2 = 0.35$
where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:
$H_2O$ 15.2 wt. %
Cyclohexane 14.6 wt. %
n-Hexane 16.7 wt. %

The surface area of the zeolite was measured to be 494 $m^2/g$.

The chemical composition of the uncalcined material was determined to be as follows:

| Component | wt. % |
| --- | --- |
| $SiO_2$ | 66.9 |

-continued

| Component | wt. % |
|---|---|
| $Al_2O_3$ | 5.40 |
| Na | 0.03 |
| N | 2.27 |
| Ash | 76.3 |
| $SiO_2/Al_2O_3$, mole ratio | 21.1 |

TABLE E

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3–5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |

TABLE F-continued

| Example | 3 | 4 | 5 |
|---|---|---|---|
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption. Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate product of Examples 3, 4 and 5 were tested in the Alpha Test and found to have Alpha Values of 227, 180 and 187, respectively.

EXAMPLE 7

To demonstrate a larger preparation of the required zeolite 1200 g of hexamethyleneimine was added to a solution containing 268 g of sodium aluminate, 267 g of 50% NaOH solution and 11,800 g of $H_2O$. To the combined solution was added 2,280 g of Ultrasil silica. The mixture was crystallized with agitation (about 200 rpm) at 145° C. in a 5 gallon reactor. Crystallization time was 59 hours. The product was water washed and dried at 120° C.

Product chemical composition, surface area and adsorption analyses results were as set forth in Table G:

TABLE G

| Product Composition (uncalcined) | | |
|---|---|---|
| C | 12.1 | wt. % |
| N | 1.98 | wt. % |
| Na | 640 | ppm |
| $Al_2O_3$ | 5.0 | wt. % |
| $SiO_2$ | 74.9 | wt. % |
| $SiO_2/Al_2O_3$, mole ratio | 25.4 | |
| Adsorption wt. % | | |
| Cyclohexane | 9.1 | |
| n-Hexane | 14.9 | |
| $H_2O$ | 16.8 | |
| Surface Area, $m^2/g$ | 479 | |

EXAMPLE 8

Twenty-five grams of solid crystal product from Example 7 were calcined in a flowing nitrogen atmospheres at 538° C. for 5 hours, followed by purging with 5% oxygen gel (balance $N_2$) for another 16 hours at 538° C.

Individual 3 g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |

| Exchange Ions Ionic Composition, wt. % | TEA | TPA | La |
|---|---|---|---|
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite were X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:
$SiO_2/B_2O_3 = 6.1$
$OH^-/SiO_2 = 0.06$
$H_2O/SiO_2 = 19.0$
$K/SiO_2 = 0.06$
$R/SiO_2 = 0.30$
where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:
$H_2O$ 11.7 wt. %
Cyclohexane 7.5 wt. %
n-Hexane 11.4 wt. %
The surface area of the calcined crystralline material was measurd (BET) to be 405 $m^2/g$.

The chemical composition of the uncalcined material was determined to be as follows:
N 1.94 wt. %
Na 175 ppm
K 0.60 wt. %
Boron 1.04 wt. %
$Al_2O_3$ 920 ppm
$SiO_2$ 75.9 wt. %
Ash 74.11 wt. %
$SiO_2/Al_2O_3$, molar ratio 1406
$SiO_2/(Al+B)_2O_3$, molar ratio 25.8

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:
$SiO_2/B_2O_3 = 12.3$
$OH^-/SiO_2 = 0.056$
$H_2O/SiO_2 = 18.6$
$K/SiO_2 = 0.056$
$R/SiO_2 = 0.30$
where R is hexamethyleneimine.

The mixture was crystallized in a stainless steel reactor, with agitation at 300° C. for 9 days. The crystalline product was filtered, washed with water and dried at 120° C. The sorption capacities of the calcined material (6 hours at 540° C.) were measured:
$H_2O$ 14.4 wt. %
Cyclohexane 4.6 wt. %
n-Hexane 14.0 wt. %
The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLE 15

This example compares the catalytic performance of the zeolite of the invention with that of zeolite HY for the alkylation of isobutane with 2-butene.

A. Preparation of the Zeolite of the Invention

The zeolite of the invention was produced by adding 4.50 parts of hexametnyleneimine to a mixture containing 1.01 parts sodium aluminate, 1.00 part 50% NaOH, 8.56 parts Ultrasil, VN3 and 44.29 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals were separated from the remaining liquid by filtration, washed with deionized $H_2O$, exchanged with ammonium and dried. A portion of this zeolite was further exchanged with aqueous solution of ammonium nitrate. The material was then dried overnight at 120° C. (250° F.), calcined at 480° C. (900° F.) for three hours in 3v/v/min $N_2$, then treated with 50 vol. % air/50 vol. % $N_2$ at 3v/v/min, also at 480° C. (900° F.) for one hour. The calcination was completed by raising the temperature to 540° C. (1000° F.) at 3° C. (5° F.)/min and finally switching to 100% air (3v/v/min) and holding at this temperature for six hours. The resultant zeolite had an alpha activity of 323, a surface area of 455 m²/g and contained 28 ppm sodium.

B. Preparation of Zeolite HY

The HY catalyst was prepared by exchanging 60 g of NaY with 1N NH$_4$NO$_3$ for one hour at room temperature. The catalyst was filtered, washed, and the exchange procedure was repeated. The ammonium exchanged Y zeolite was calcined in air for three hours at 540° C. (1000° F.). The final material had an alpha activity of 61, a surface area of 721 m²/g, and contained 3.0 wt. % sodium.

C. Alkylation of Isobutane With 2-Butene

To assess the catalytic properties of the above zeolites, separate alkylation runs were carried out batchwise in an autoclave. The start-up procedure included the charging of 10 grams of catalyst into the reactor followed by sealing of the vessel. Approximately 350 grams of isobutane/2-butene were then introduced into the autoclave and the slurry was stirred during the subsequent nitrogen pressure test. To commence the reaction, nitrogen pressure was lowered to 1135 kPa (150 psig), and the system heated at a rate of 3° C. (5° F.)/minute. The final reaction conditions in each run were a temperature of 120° C. (250° F.), autogeneous pressure 3410 kPa or (480 psig), and a stirring speed of 500 rpm.

The results of the alkylation runs are set forth in Table H as follows:

TABLE H

| Alkylation Conditions Catalyst | Invention | Invention | HY | HY |
|---|---|---|---|---|
| iC$_4$/2-C$_4$ = Mole Ratio | 50 | 10 | 50 | 10 |
| Hours on Stream | 76 | 49 | 28 | 46 |
| Conversion (%) | 95 | 73 | 99 | 85 |
| Product Distribution | | | | |
| C$_5$ | 1.5 | 0.6 | 1.8 | 1.7 |
| C$_6$ | 4.9 | 3.4 | 5.0 | 3.3 |
| C$_7$ | 3.9 | 2.2 | 7.1 | 5.7 |
| C$_8$ | 74.4 | 63.1 | 43.0 | 36.0 |
| C$_9$+ | 15.4 | 30.8 | 43.2 | 53.3 |
| Distribution of C$_8$ Products | | | | |
| 2,2,4-trimethylpentane | 4.4 | 1.0 | 8.1 | 2.9 |
| 2,3,3-trimethylpentane | 43.1 | 31.8 | 18.3 | 8.4 |
| 2,3,4-trimethylpentane | 34.5 | 21.7 | 14.2 | 7.7 |
| Dimethylhexanes | 16.3 | 25.3 | 56.6 | 69.7 |
| Other product(s) | 1.8 | 20.3 | 2.8 | 11.2 |
| Dimethylhexanes Mole Ratio | 5.0 | 2.2 | 0.7 | 0.3 |

As these data show, the use of the alkylation catalyst of the invention resulted in substantially more trimethylpentane alkylate and significantly less C$_9$+products compared to the use of zeolite HY catalyst under equivalent conversion conditions.

What is claimed is:

1. An isoparaffin-olefin alkylation process which comprises reacting isoparaffin and olefin under alkylation conditions providing an alkylate product in the presence of, as catalyst, a zeolite characterized by an X-ray diffraction pattern including values substantially as set forth below:

| Interplanar d-Spacing (A) | Relative Intensity, I/I$_o$ × 100 |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS. |

2. The process of claim 1 wherein the zeolite is characterized by an X-ray diffraction pattern including values substantially as set forth below:

| Interplanar d-Spacing (A) | Relative Intensity, I/I$_o$ × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS. |

3. The process of claim 1 wherein the zeolite is characterized by an X-ray diffraction pattern including values substantially as set forth below:

| Interplanar d-Spacing (A) | Relative Intensity, I/I$_o$ × 100 |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W. |

4. The process of claim 1 wherein the zeolite is characterized by an X-ray diffraction pattern including values substantially as set forth below:

| Interplanar d-Spacing (A) | Relative Intensity, I/I$_o$ × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |

-continued

| Interplanar d-Spacing (A) | Relative Intensity, $I/I_o \times 100$ |
|---|---|
| 4.64 ± 0.08 | W |
| 4.41 ± 0.08 | W–M |
| 4.25 ± 0.08 | W |
| 4.10 ± 0.07 | W–S |
| 4.06 ± 0.07 | W–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W. |

5. The process of claim 1 wherein the zeolite has a composition comprising the molar relationship $$X_2O_3:(n)YO_2,$$

wherein n is at least about 10, X is a trivalent element and Y is a tetravalent element.

6. The process of claim 1 wherein the zeolite possesses equilibrium adsorption capacities of greater than about 4.5 wt. % for cyclohexane vapor and greater than about 10 wt. % for n-hexane vapor.

7. The process of claim 5 wherein X is selected from the group consisting of aluminum, boron, gallium and combinations thereof and Y is selected from the group consisting of silicon, geranium and combinations thereof.

8. The process of claim 5 wherein X is aluminum and Y is silicon.

9. The process of claim 1 wherein the zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

10. The process of claim 1 wherein the catalyst has been thermally treated at a temperature up to about 1700° F. in the presence or absence of steam.

11. The process of claim 9 wherein the catalyst has been thermally treated at a temperature up to about 1700° F. in the presence or absence of steam.

12. The process of claim 1 wherein the isoparaffin contains from 4 to about 8 carbon atoms and the olefin contains from 2 to 12 carbon atoms.

13. The process of claim 1 wherein the isoparaffin is isobutane and the olefin is propylene and/or butene(s).

14. The process of claim 1 wherein the reaction is carried out under sufficient pressure to maintain at least one of the reactants in the liquid phase.

15. The process of claim 1 wherein the isoparaffin and olefin are present as supercritical fluids.

16. The process of claim 1 wherein the mole ratio of total isoparaffin to total olefin is from about 1:2 to about 100:1.

17. The process of claim 1 wherein the mole ratio of total isoparaffin to total olefin is from about 3:1 to about 30:1.

18. The process of claim 1 wherein the alkylation reaction temperature is from about −25° C. to about 400° C., the pressure is from below atmospheric to about 5000 psig and the weight hourly space velocity based on olefin is from about 0.01 to 100 $hr^{-1}$.

19. The process of claim 1 wherein the alkylation reaction temperature is from about 75° C. to about 200° C., the pressure is from atmospheric to about 1000 psig and the weight hourly space velocity of the olefin is from about 0.1 to about 20 $hr^{-1}$.

20. The process of claim 1 conducted in the presence of hydrogen and/or a hydrogen donor.

21. The process of claim 1 conducted in the presence of water and/or a material which provides water under reaction conditions.

22. The process of claim 1 conducted in the presence of an olefin oligomerization supressant.

23. The process of claim 1 wherein said zeolite is combined with a matrix material.

24. The process of claim 23 wherein said matrix material is selected from the group consisting of silica-containing material, alumina-containing material, zirconia-containing material, titania-containing material, magnesia-containing material, beryllia-containing material, thoria-containing material, and combinations thereof.

* * * * *

UNITED STATES PATENT AND TRADEMARK OFFICE
CERTIFICATE OF CORRECTION

PATENT NO. : 4,992,615

DATED : February 12, 1991

INVENTOR(S) : A. Huss, Jr.

It is certified that error appears in the above-identified patent and that said Letters Patent is hereby corrected as shown below:

```
Col. 1, line 43, "alxylation " should be --alkylation--.
Col. 2, line 9, insert --with-- after "isoparaffins".
Col. 9, line 42, "alxylation" should be --alkylation--.
Col. 9, line 66, "cyclonexane" should be --cyclohexane--.
Col. 14, line 52,  "hexametnyleneimine" should be
                    --hexamethyleneimine--.
Col. 15, line 51, "Dimethylhexanes Mole Ratio" should be
                   --Trimethylpentanes/Dimethylhexanes
                     Mole Ratio--.
Col. 18, claim 21, line 34, insert --the-- after "under".
```

Signed and Sealed this

Seventh Day of July, 1992

Attest:

DOUGLAS B. COMER

*Attesting Officer*  *Acting Commissioner of Patents and Trademarks*